(12) United States Patent
Wang et al.

(10) Patent No.: US 6,461,328 B2
(45) Date of Patent: Oct. 8, 2002

(54) SAFETY SYRINGE

(75) Inventors: Lin Wang, Hsi Chih; Chung-Hsin Yang, San Chung, both of (TW)

(73) Assignee: Uniqsafe Medical Technology Group Ltd., Tortola (VG)

( * ) Notice: Subject to any disclaimer, the term of this patent is extended or adjusted under 35 U.S.C. 154(b) by 112 days.

(21) Appl. No.: 09/746,482

(22) Filed: Dec. 26, 2000

(65) Prior Publication Data

US 2002/0082555 A1 Jun. 27, 2002

(51) Int. Cl.[7] ............................. A61M 5/32; A61M 5/50
(52) U.S. Cl. ..................................................... 604/110
(58) Field of Search ........................................ 604/110

(56) References Cited

U.S. PATENT DOCUMENTS

| | | | | |
|---|---|---|---|---|
| 5,575,774 A | * | 11/1996 | Chen | 604/110 |
| 5,687,740 A | * | 11/1997 | Sheridan | 604/195 |
| 5,693,023 A | * | 12/1997 | Shillinton | 604/187 |
| 6,162,197 A | * | 12/2000 | Mohammed | 604/195 |
| 6,196,997 B1 | * | 3/2001 | Saito | 604/110 |

* cited by examiner

*Primary Examiner*—Paul J. Hirsch
(74) *Attorney, Agent, or Firm*—Jacobson Holman, PLLC (57) ABSTRACT

A safety syringe has a retaining device formed on a front end of the barrel, multiple bosses formed on the needle hub to rotatably correspond to the retaining device, multiple recesses defined inside the needle hub and multiple inclined teeth formed on the plunger to correspond to the recesses, such that the engagement between the retaining device and the bosses of the needle hub is able to be released by the rotational movement of the plunger together with the needle hub due to the combination of the inclined teeth and the recesses.

3 Claims, 8 Drawing Sheets

SAFETY SYRINGE

BACKGROUND OF THE INVENTION

1. Field of the Invention

The present invention relates to a syringe, and more particularly to a safety syringe, which has a ratchet device formed on the needle hub and an annular inclined teeth formed on one end of the plunger, such that when the hollow barrel is pushed toward the needle hub, the engagement between the ratchet device and the inclined teeth is able to pull the needle hub together with the needle inside the barrel when the barrel is pulled backward to prevent people from being punctured by the used needle.

2. Description of Related Art

A plastic cap is always mounted on the hollow barrel of a syringe to cover the needle to keep people from being punctured by the used needle. However, because the user must hold the conventional cap when he or she puts the cap onto the hollow barrel, the user is easily punctured by the needle. In addition, the used needle must be destroyed by melting or burning to prevent the spread of disease. However, hazardous gas will form when the needle with the plastic cap and needle hub is melted or burned.

In another conventional embodiment, a safety device is formed with the syringe to prevent the user from being punctured. Clamps are formed on the needle hub and the plunger of the syringe. When the plunger is fully pushed into the hollow barrel of the syringe, the clamps will engage with each other. The needle hub with the needle will release from and be pulled fully into the barrel when the plunger is pulled back. The used needle will be fully enclosed and held in the hollow barrel to keep the needle from touching or puncturing anyone.

However, a specific mold is required to form the clamps. The cost for manufacturing the syringe with the conventional safety device is expensive. In addition, because the entire syringe including the hollow barrel, plunger and the hub must be melted or burned with the needle, hazardous gas is still generated.

Figure 1:
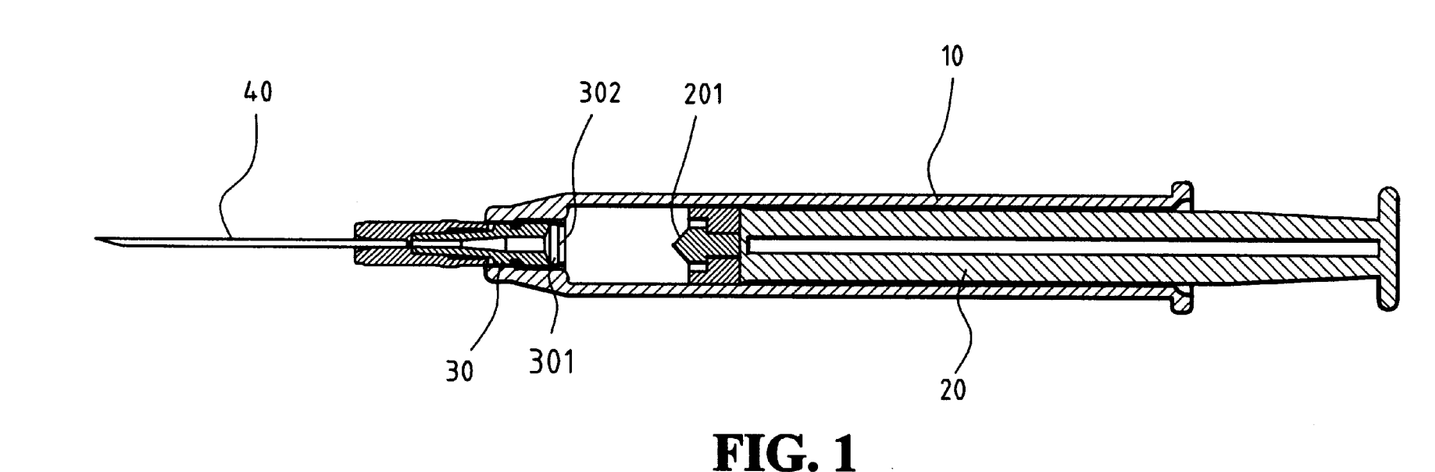
FIG. 1 is a cross sectional view of a conventional syringe.

In order to reduce the fabrication cost, the market focuses on the development to introduce an improved syringe to pull the used needle inside the barrel. With reference to FIG. 1, a conventional safety syringe comprises a hollow barrel (10), a plunger (20), a needle hub (30) and a needle (40).

Figure 2:
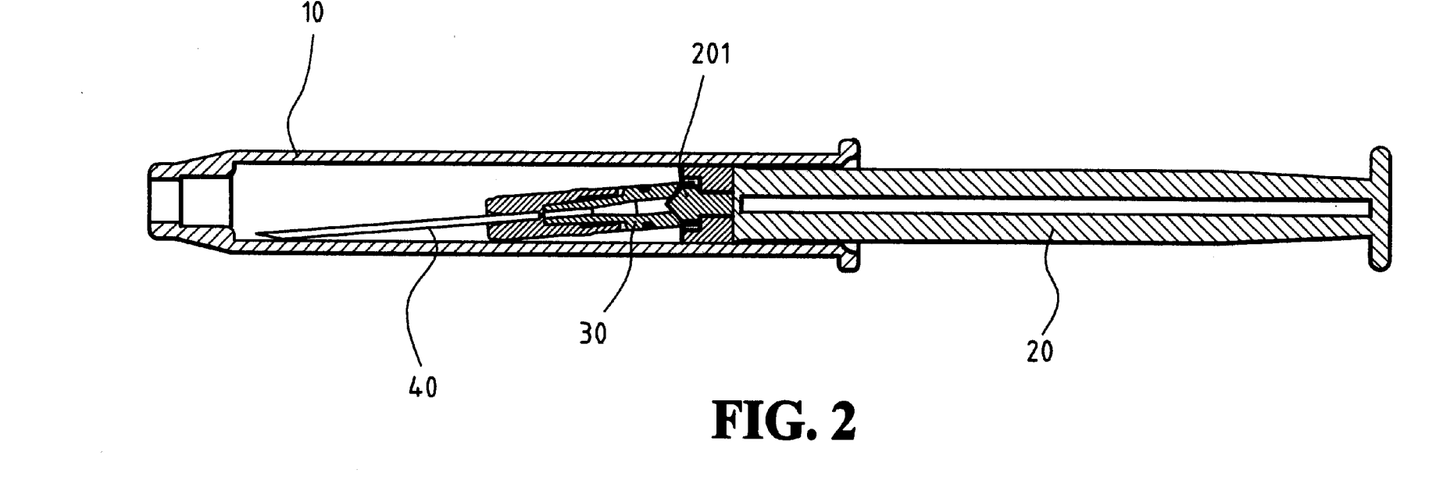
FIG. 2 is a cross sectional view of the syringe of FIG. 1, wherein the needle hub is pulled back into the barrel.

The needle hub (30) defines a receiving hole (301) in a rear end of the needle hub (30) and a shoulder (302) is formed inside the receiving hole (301). The plunger (20) has a conical head (201) formed on a front end of the plunger (20) to correspond to the receiving hole (301). With this arrangement, when the plunger (20) is moving inside the barrel (10) toward the needle hub (30) and eventually engages with the needle hub (30), the conical head (201) will have an interference fit inside the receiving hole (301). Because the formation of the shoulder (302), the conical head (201) is secured inside the receiving hole (301) after the plunger (20) is pushed all the way to the end of the hollow barrel (10), such that when the plunger (20) is pulled backward inside the barrel (10), the needle hub (30) together with the needle (40) is able to be pulled inside the barrel (10) simultaneously, as shown in FIG. 2.

However, to facilitate the needle hub (30) to be pulled inside the barrel (10), the engagement between the needle hub (30) and the barrel (10) should be loose otherwise the friction between the needle hub (30) and an inner periphery of the barrel (10) will overcome the connection between the plunger (20) and the needle hub (30) and the needle hub (30) can not be pulled back into the barrel (10) successfully. In the mean time, if the engagement between the needle hub (30) and the barrel (10) is loose, the solution inside the barrel will have a leak and the injection can not be successful. Further, when the needle (40) is inserted into a container (50) through the cork (51), the needle hub (30) may retract back into the barrel (10). However, if the engagement between the needle hub (30) and the barrel (10) is increased, the force required to pull the needle hub (30) together with the needle (40) back to the barrel (10) is also increased, which causes an extra burden to the users.

Figure 5:
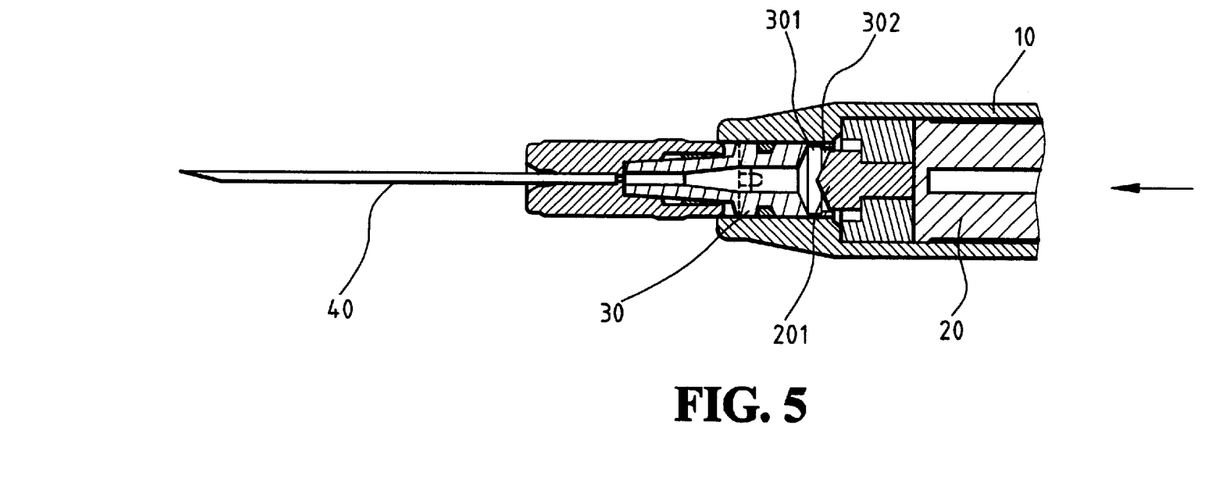

With reference to FIG. 5, whether reducing the diameter of the receiving hole (301) or increasing the diameter of the conical head (201) to increase the engagement force between the needle hub (30) and the barrel (10) will inevitably increase the difficulty of inserting the conical head (201) into the receiving hole (301) and this is the last thing that the user wants to see.

To overcome the shortcomings, the present invention intends to provide an improved safety syringe to mitigate or obviate the aforementioned problems.

SUMMARY OF THE INVENTION

The primary objective of the invention is to provide a syringe enabling to release the limitation of the barrel to the needle hub so that the needle hub with the needle is able to be pulled backward into the barrel easily.

Another objective of the invention is to provide a syringe that is able to provide a seal to the solution inside the barrel by the engagement between the needle hub and the barrel, such that there is no leak even though the needle hub is slidably engaged with the barrel.

Still, another objective of the invention is to provide an improved syringe with a ratchet device formed on one end of the needle hub and inclined teeth formed on one end of the plunger to correspond to the ratchet device of the needle hub, such that the engagement between the ratchet device and the inclined teeth will facilitate the retraction of the needle hub together with the needle back into the barrel.

Other objects, advantages and novel features of the invention will become more apparent from the following detailed description when taken in conjunction with the accompanying drawings.

DETAILED DESCRIPTION OF PREFERRED EMBODIMENT

Figure 6:
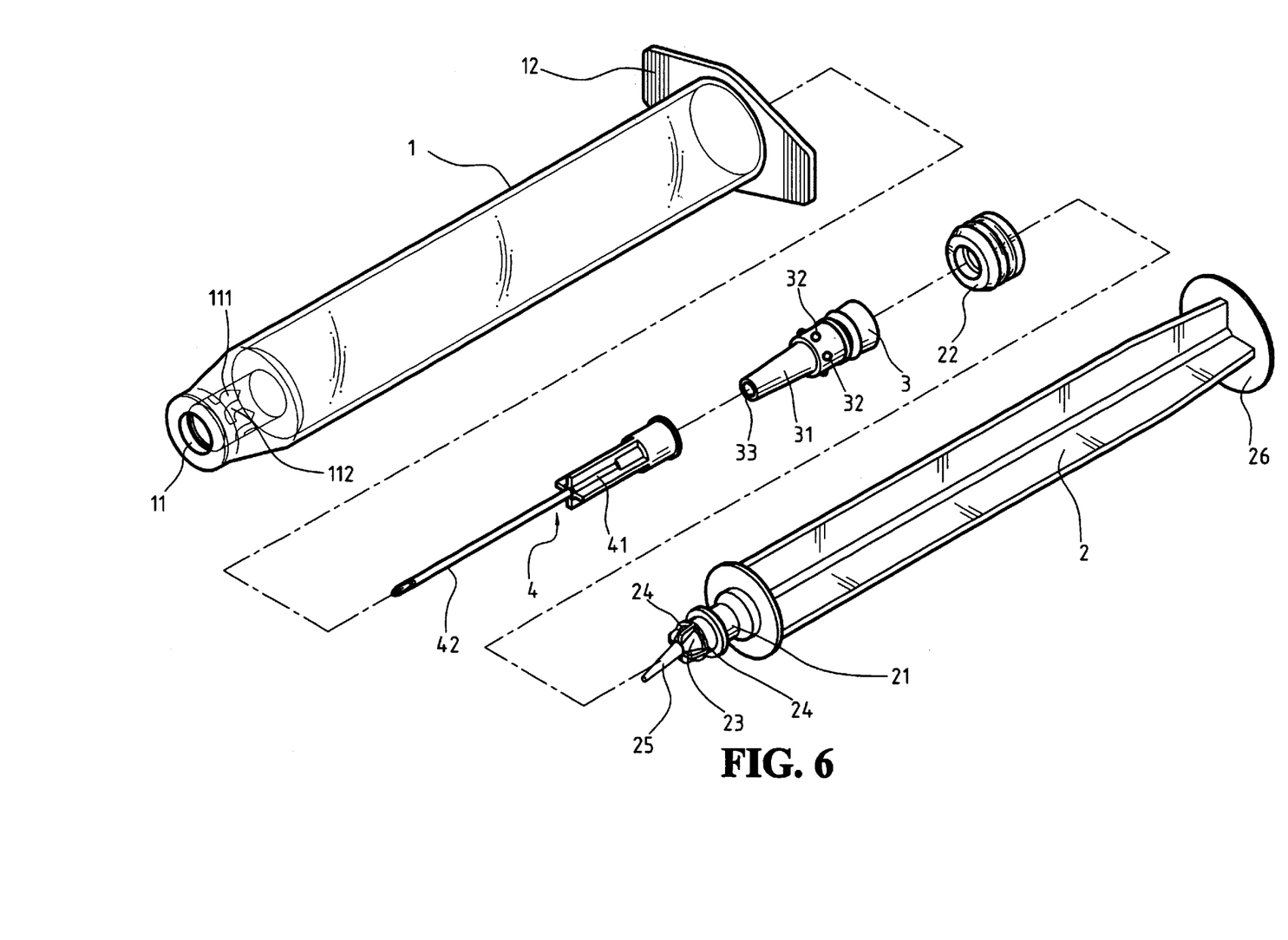
FIG. 6 is an exploded perspective view of a syringe in accordance with the present invention.

With reference to FIG. 6, a syringe in accordance with the present invention has a barrel (1), a plunger (2), a needle hub (3) and a needle (4).

Figure 7:
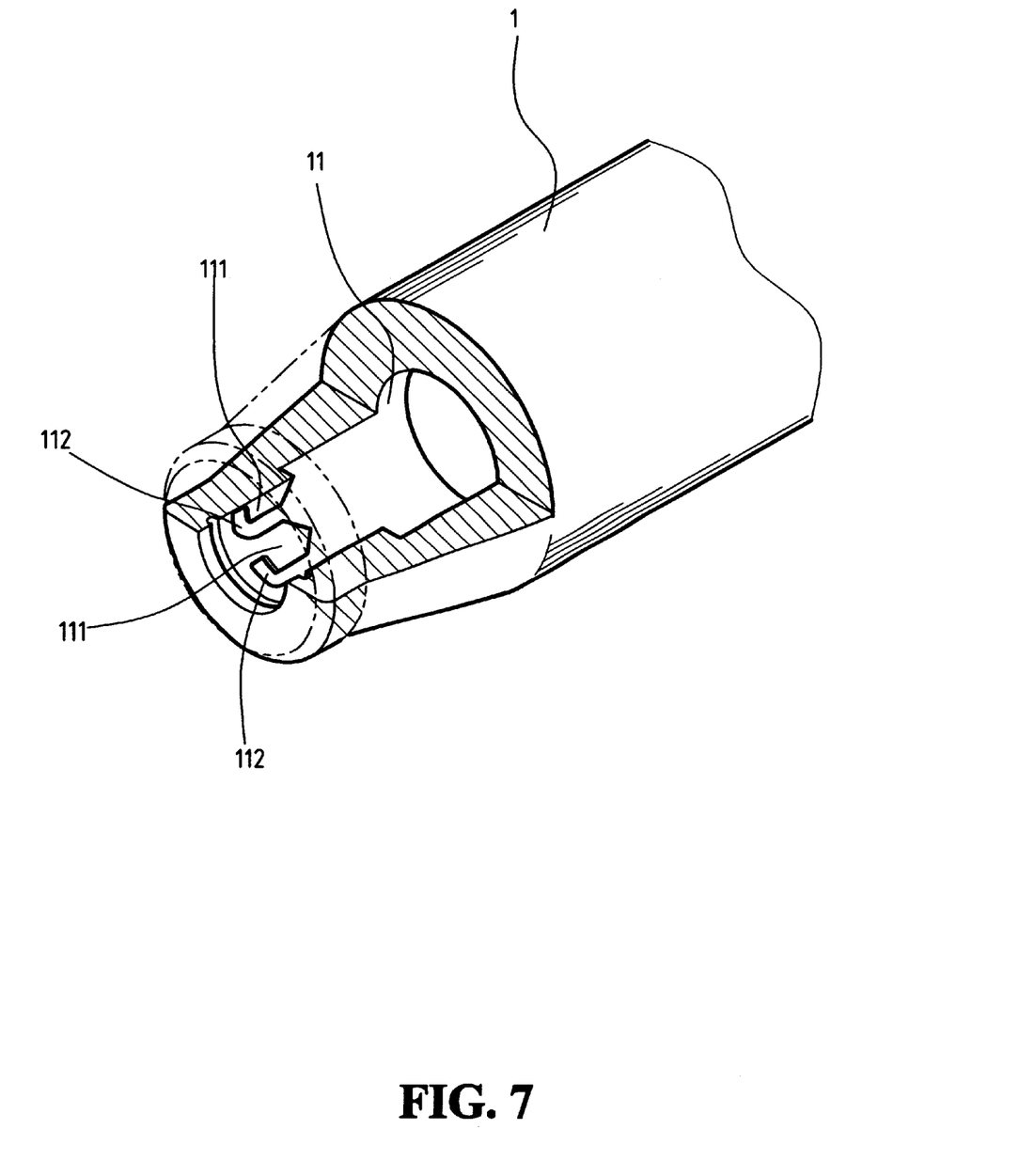
FIG. 7 is a partially sectioned and enlarged perspective view of the front end of the barrel in accordance with the present invention.

As shown in FIGS. 6 and 7, the barrel (1) defines axially therein a through hole (11) and has a retaining device (110) formed on a front end of the barrel. The retaining device has multiple equally-spaced fingers (111) formed on an inner periphery defining the through hole (11) and troughs (112) each defined between two adjacent fingers (111). Each of the fingers are L shaped hence each of the troughs (112) are also L shaped.

With reference to FIG. 6 again, the plunger (2) has a neck (21) formed on a front end thereof so as to allow a rubber seal (22) to fit in, a conical head (23) projecting from the neck (21), multiple spatially formed inclined teeth (24), a resilient push rod (25) formed on an end of the conical head (23) and a flange (26) oppositely formed on the plunger (2) to the resilient push rod (25).

Figure 8:
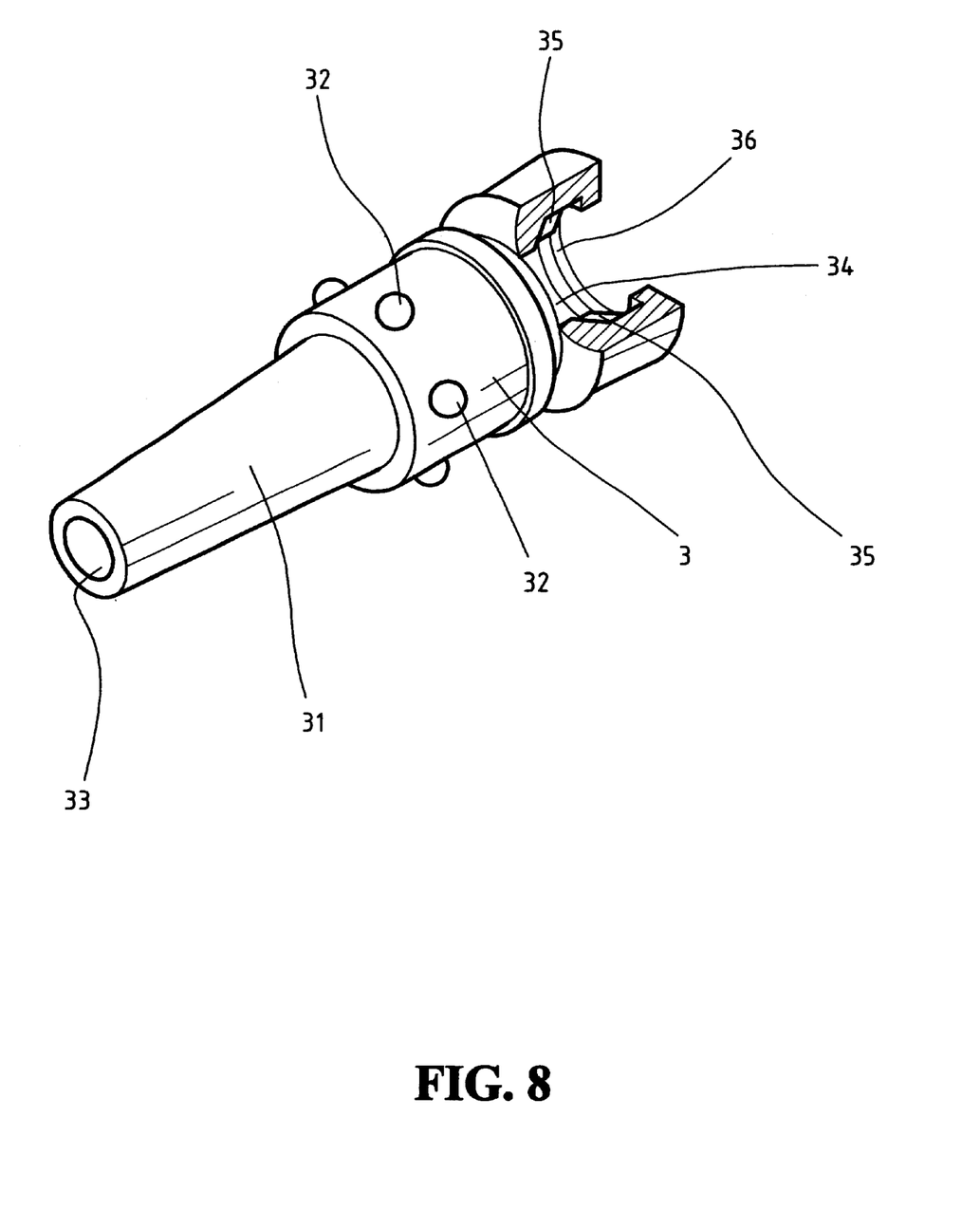
FIG. 8 is a partially sectioned and enlarged perspective view of the needle hub in accordance with the present invention.

With reference to FIGS. 6 and 8, the needle hub (3) has a conical front end (31), multiple bosses (32) formed on a periphery of the front end (31) to correspond to the troughs (112) of the barrel (1), an axially defined hole (33), a receiving hole (34) defined to communicate with the hole (33), multiple recesses (35) defined in a periphery of the receiving hole (34) to correspond to the inclined teeth (24) and a shoulder (36) defined in the periphery of the receiving hoe (34) and above the recesses (35) to correspond to the conical head (23) of the plunger (2).

The needle (4) comprises a sleeve (41) and a metal tube (42).

Figure 3:
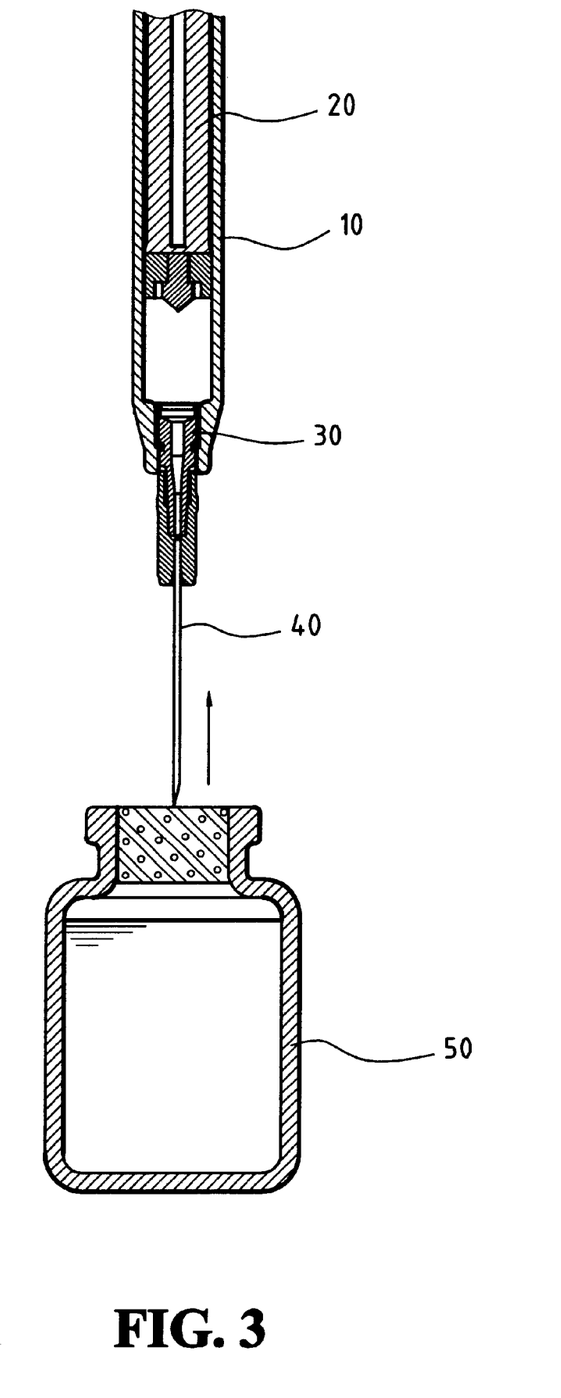
FIG. 3 is a schematic view showing that the needle hub together with the needle is pushed backward into the barrel due to the loose connection between the needle hub and the barrel.
Figure 4:
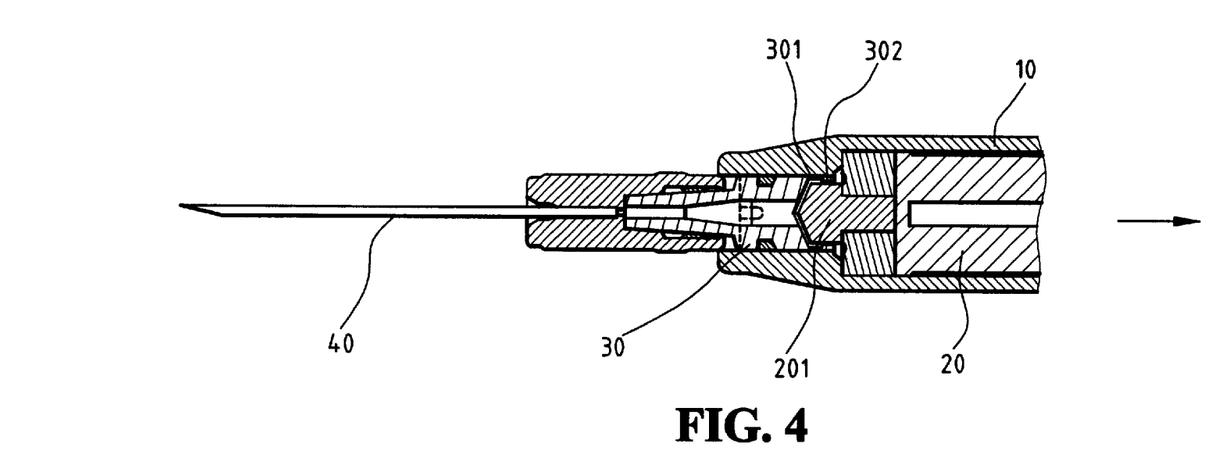
FIGS. 4 and 5 are cross sectional views showing that the configuration of the conical head or the receiving hole is changed to increase the connection between the barrel and the needle hub.

When the syringe of the invention is assembled, the needle hub (3) is inserted into the sleeve (41) of the needle (4) to have an interference fit with the needle (4). Then, the needle hub (3) together with the needle (4) is inserted into the barrel (1) to allow each of the bosses (32) to be received in a corresponding one the troughs (112) and clamped by the L shaped fingers (111). By doing do, a rotation to the needle hub (3) and the needle (4) has to be implemented so that the bosses (32) are able to be received in the troughs (112). With such an arrangement, the needle hub (3) together with the needle (4) is able to have a secure connection with the barrel (1). A worry that the needle hub (3) and the needle (4) may be pushed inside the barrel (1) while the needle is inserted into the cork (51) of FIG. 3 is avoided. When the syringe in accordance with the present invention is in use, the user inserts the plunger (2) into the barrel (1). Due to the rubber seal (22) securely received in the neck (21) of the plunger (2), the medical solution inside the barrel (1) is able to be completely injected out of the barrel (1).

Figure 9:
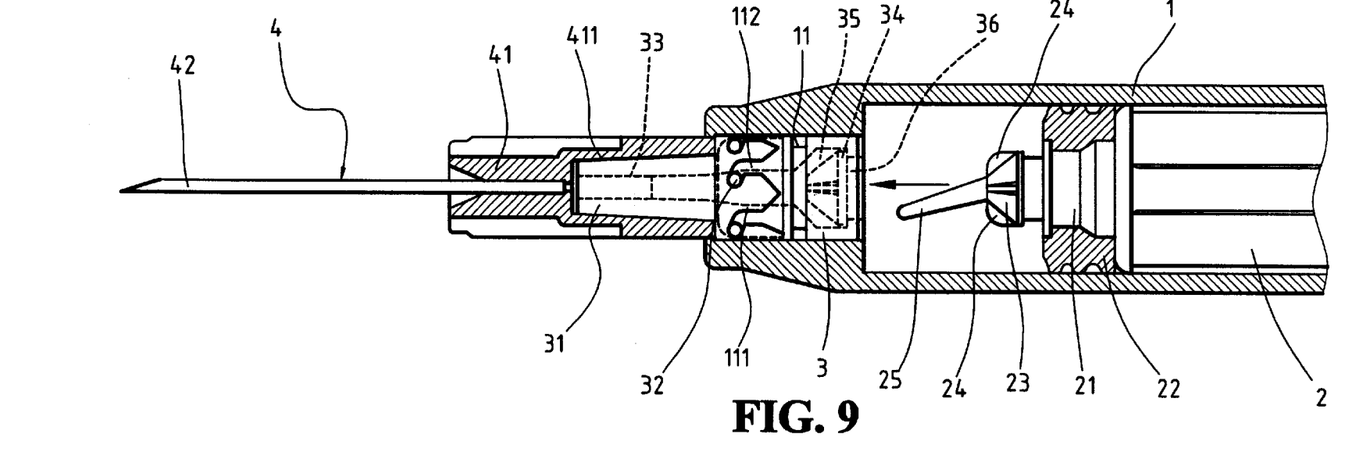
FIGS. 9 and 10 are cross sectional side views showing the movement of the plunger inside the barrel to connect with the needle hub.
Figure 10:
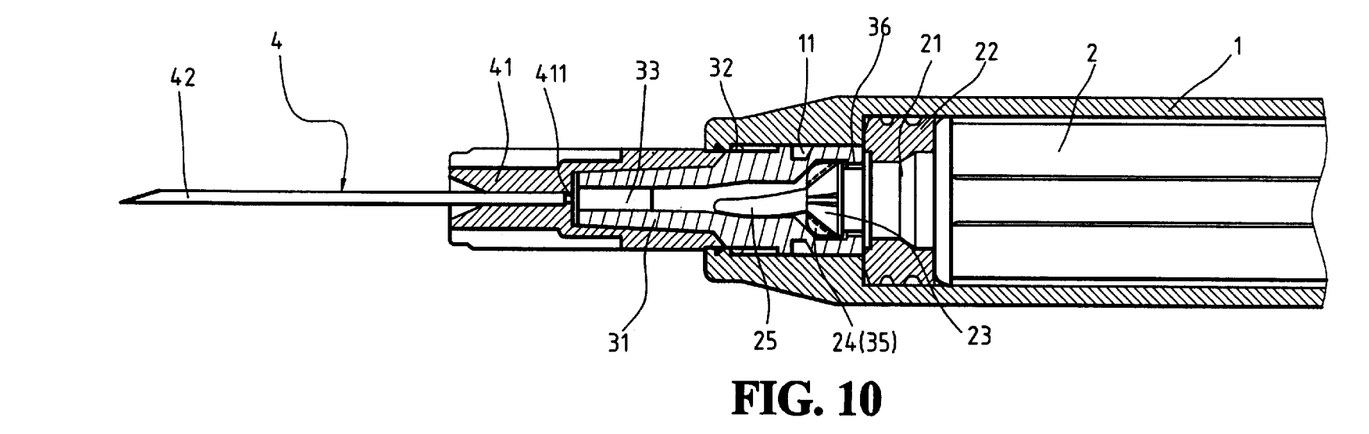

With reference to FIG. 9, after the solution is empty inside the barrel (1), the user continuously pushes the plunger (2) to force the conical head (23) and the. push rod (25) to extend into the receiving hole (34) and thus allows the resilient push rod (25) to rest inside the inner periphery of the hole (33). When the conical head (23) of the plunger (2) extends into the receiving hole (34), the inclined teeth (24) is received in the recesses (35) and the joint between the neck (21) and the conical head (23) engages the shoulder (36), as shown in FIG. 10.

Figure 11:
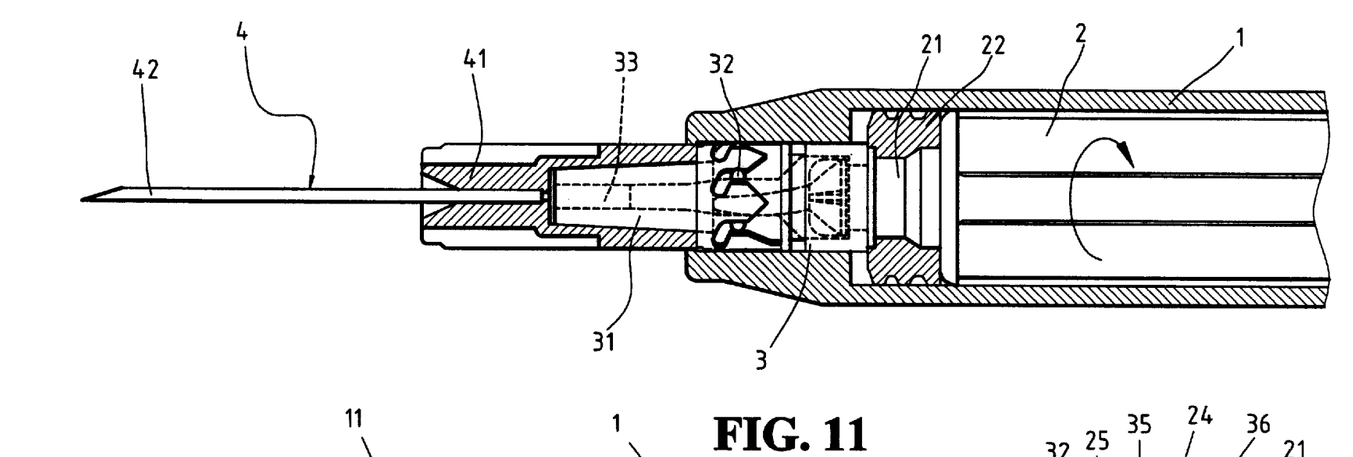
FIG. 11 is a cross sectional side plan view showing the rotation of the plunger to securely connect with the needle hub.

Thereafter, with reference to FIG. 11, the user rotates the plunger (2) to allow the engagement between the inclined teeth (24) and the recesses (35) to simultaneously rotate the needle hub (3) to release the limitation of the L shaped fingers (111) to the bosses (32). After the limitation of the fingers (111) to the bosses (32) is released, the engagement of the conical head (23) to the shoulder (36) enables the user to pull the needle hub (3) together with the needle (4) back into the barrel (1).

Figure 12:
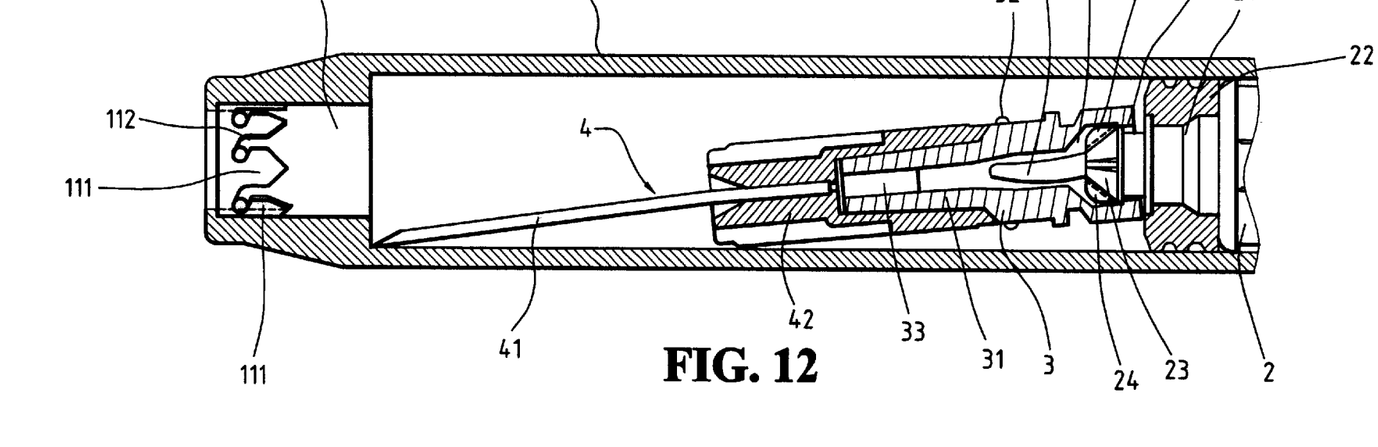
FIG. 12 is a cross sectional side plan view showing the needle hub together with the needle is pulled backward into the barrel.

With reference to FIG. 12, when the needle hub (3) together with the needle (4) is pulled back into the barrel (1), the resilient push rod (25) will press against the needle hub (3) together with the needle (4) to offset the alignment of the needle hub (3) together with the needle (4) to the through hole (11) of the barrel (1), such that a reuse to the syringe is impossible.

Even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A safety syringe comprising:

a barrel having a through hole axially defined therein and a retaining device formed inside a front end of the barrel;

a plunger slidably received in the barrel and having a neck formed on a front end thereof so as to allow a rubber seal to fit in, a conical head projecting from the neck, multiple spatially formed inclined teeth, and a flange oppositely formed on the plunger to conical head;

a needle hub detachably engaged with the barrel and having a conical front end with multiple bosses formed to rotatably correspond to the retaining device of the barrel, an axially defined hole corresponding to and being in communication with the through hole of the barrel, a receiving hole defined to communicate with the hole and the through hole of the barrel and to allow the extension of the conical head of the plunger, multiple recesses defined to receive the inclined teeth and a shoulder defined in a periphery of the receiving hole to correspond to the conical head of the plunger; and a needle having a sleeve securely engaged with the conical front head of the needle hub and a metal tube securely engaged with the sleeve;

wherein the bosses are rotatably released from the clamp of the fingers by the engagement of the inclined teeth and the recesses.

2. The syringe as claimed in claim 1, wherein the retaining device comprises multiple L shaped fingers formed to clamp the bosses and multiple troughs defined to receive the bosses.

3. The syringe as claimed in claim 2, wherein a resilient push rod is formed on an end of the conical head to be received in and abutted to an inner periphery of the receiving hole of the needle hub.

* * * * *